United States Patent [19]

Takeuchi et al.

[11] Patent Number: 4,713,469

[45] Date of Patent: Dec. 15, 1987

[54] FLUORINE-CONTAINING MULTIFUNCTIONAL ESTER COMPOUND

[75] Inventors: Yoshio Takeuchi, Kosugi; Toru Koizumi, Toyama; Kozo Hori, Kosui, all of Japan

[73] Assignee: Daikin Industries, Ltd., Osaka, Japan

[21] Appl. No.: 845,106

[22] Filed: Mar. 27, 1986

Related U.S. Application Data

[63] Continuation-in-part of Ser. No. 808,564, Dec. 13, 1985, abandoned.

[30] Foreign Application Priority Data

Mar. 1, 1985 [JP] Japan .................................. 60-41619
Mar. 1, 1985 [JP] Japan .................................. 60-41620

[51] Int. Cl.[4] ...................... C07C 117/00; C07C 69/14
[52] U.S. Cl. ........................................ 560/17; 260/349; 560/153; 560/156; 560/227
[58] Field of Search ........................ 560/227, 17, 153; 260/349

[56] References Cited

PUBLICATIONS

Filler, et al.; Biomedical Aspects of Fluorine Chemistry; (1982); chapter by Kollonitsch, pp. 93–122, [Elsevier Biomed. Press Amsterdam, N.Y., Oxford].
Atkinson; et al, J. Chem. Soc., (1949), pp. 1040–1041.
Sarel; Accts. of Chem. Research, (1978), p. 204.
Lyttle, et al.; J.A.C.S. (1949), pp. 2118–2119.
Kobayashi, et al., Accts. of Chem Research (1978), pp. 197–203.
C.A., 72; 21459h; Kuliev, et al, (1970).
C.A., 73; 3220q; Peterson, et al, (1970).
C.A., 77; 125889t; Boguslavskaya, et al, (1972).
C.A., 81; 2997b; Jones, et al., (1974).
C.A., 81; 77294d; Clene, (1974).
C.A., 81; 77432x; Peterson, et al., (1974).
C.A., 88; 136105n; Peterson, et al., (1978).
C.A., 99; 22024g; Stanber, et al., (1983).
C.A., 101; 170567m; Balahan, et al., (1984).

*Primary Examiner*—Joseph Paul Brust
*Attorney, Agent, or Firm*—Murray and Whisenhunt

[57] ABSTRACT

A fluorine-containing multifunctional ester compound represented by the formula

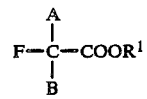

wherein A is halogen atom, $NO_2$ or $N_3$, B is halogen atom or $SR^2$, $R^1$ is lower aliphatic group, aromatic group or aralkyl, $R^2$ is lower aliphatic group or aromatic group.

2 Claims, No Drawings

FLUORINE-CONTAINING MULTIFUNCTIONAL ESTER COMPOUND

The present application is a continuation-in-part of application Ser. No. 808,564 filed Dec. 13, 1985, now abandoned.

The invention relates to a fluorine-containing multifunctional ester compound.

Research on compounds containing a carbon atom having at least three different functional groups has drawn a great interest in the field of organic synthesis. These compounds are useful, for example, for synthesis of an optical isomer based on the multifunctional groups, for asymmetric synthesis, for synthesis of organic fluorine compounds as used for fluorine-containing synthon, etc.

An object of the invention is to provide a novel compound having a multifunctional carbon atom.

The above and other objects will become apparent from the following description.

The invention provides a fluorine-containing multifunctional ester compound represented by the formula

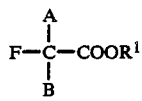

wherein A is halogen atom, $NO_2$ or $N_3$, B is halogen atom or $SR^2$, $R^1$ is lower aliphatic group, aromatic group or aralkyl, $R^2$ is lower aliphatic group or aromatic group.

The compound of the invention has functional groups such as carbonyl, halogen and mercapto, and is useful, for example, for synthesis of an optical isomer based on the multifunctional groups, for asymmetric synthesis, for synthesis of organic fluorine compounds as used for fluorine-containing synthon, etc.

For instance, the compounds of the present invention can be used to synthesize antimicrobial agents. For example, the compound of the following formula:

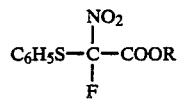

wherein R is a lower aliphatic group, can be converted into β-fluoroalanine, a known antimicrobial agent (Biomedical Aspects of Fluorine Chemistry, P. 93–96 (1982), Elsevier Biomedical Press).

The conversion of the compound of the above formula into β-fluoroalanine is by the following procedure:

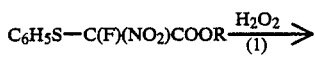

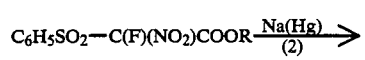

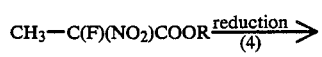

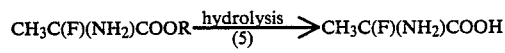

Steps 1 and 2 are conducted according to the procedures of Y. Kobayashi, I. Kumadaki, Acc. Chem. Res., 11, 197 (1978).

Step 3 is conducted according to the procedure of R. O. Atokinson, P. A. A. Scott, J. Chem. Soc., (1949) 1040. Steps 4 and 5 are conducted according to the procedure of D. A. Lyttle, D. I. Weisblat, J. Am. Chem. Soc., 69, 2118 (1947).

Examples of the preferred aliphatic groups in $R^1$ and $R^2$ are methyl, ethyl, propyl and like alkyl groups having 1 to 4 carbon atoms. Examples of useful aromatic groups are phenyl, p-chlorophenyl, tolyl, xylyl, naphthyl, etc. Aralkyl groups in $R^1$ include benzyl, phenethyl and the like. Examples of halogen atoms in A and B are fluorine, chlorine, bromine and iodine.

The present compound can be prepared, for example, by substituting hydrogen atom bonded to α-carbon atom of the corresponding ester with halogen atom or mercapto group. The compound of the invention can also be obtained by substituting bromine atom bonded to the above α-carbon atom with azido group. Halogenizing agents include known agents such as $F_2$, perchloryl fluoride, N-bromosuccinimide, etc. Examples of agents for introducing a mercapto group are thiophenol, phenylsulfenyl chloride and like known agents. Examples of agents for providing an azido group are sodium azide and like usual agents.

More specifically stated, the present compound can be prepared by reacting an ester of the formula

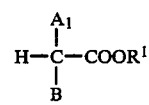

with a fluorinating agent.

The present compound is prepared by reacting an ester of the formula

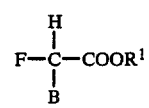

with a halogenizing agent other than fluorinating agent.

The present compound is also prepared by reacting an ester of the formula

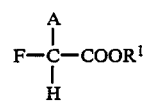

with an agent for introducing a mercapto group.

The present compound is further prepared by reacting an ester of the formula

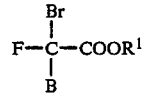

with an agent for providing an azido group.

In the above, A, B, R[1] and R[2] are the same as defined above, and $A_1$ is Cl, Br, I or $NO_2$.

In the invention, the above reaction of the corresponding ester and a reagent is conducted preferably in an organic solvent. Examples of organic solvents are carbon tetrachloride, ethyl acetate, tetrahydrofuran and the like. In the reaction, it is preferable to use about 1.0 to 10 moles of the reagent per mole of the starting substance. The reaction temperature and reaction time are preferably selected from the range of about 0° to 80° C. and about 2 to 48 hours respectively.

The present compound can be isolated and purified by a known method such as extraction, distillation, concentration, recrystallization, gas chromatography, column chromatography, etc.

The invention will be described in more detail with reference to the following examples.

EXAMPLE 1

Into a 100-ml flask were placed 1.442 g (6 m moles) of ethyl nitro(phenylthio)acetate and 20 ml of ethanol. With introducing ammonia gas thereto for 5 minutes, precipitates immediately formed. Ethanol and excess ammonia were removed by an evaporator to obtain ammonium salt as the residue. To the residue were added 50 ml of water and 5 ml of chloroform and the solution was cooled on an ice-bath. To the solution was gradually introduced 10% $F_2/N_2$ gas with stirring. The reaction mixture was checked several times and, when the mixture was acidic, was made alkaline by adding a few droups of 28% aqueous ammonia solution. After introducing the gas for 3 hours in total, the mixture was made acidic (pH=1) with 10% hydrochloric acid and extracted with addition of 15 ml of chloroform. The aqueous layer was further extracted twice each with addition of 20 ml of chloroform. The organic layer combined was dried over magnesium sulfate and the solvent was removed to obtain 1.313 g of a yellow oily product. The product was purified by a column chromatography (Merck Art 7734, solvent: n-hexane:ethyl ether=9:1) to obtain 0.220 g (14.2%) of ethyl fluoronitro(phenylthio)acetate.

IR (neat, $cm^{-1}$) 1760 (CO), 1580 ($NO_2$), $^1$HNMR($CDCl_3$, TMS) δ 1.36 (3H, t, J=7 Hz, $CH_3$), 4.42 (2H, q, J=7 Hz, $CH_2$), 7.50 (5H, m, Ar), $^{13}$CNMR($CDCl_3$, TMS) ppm 13.7 ($CH_3$), 65.1 ($CH_2$), 119.3 (C—F), 123.7, 129.7, 131.5, 136.5 (Ar), 159.3 (C=O), $^{13}$FNMR($CDCl_3$, $CFCl_3$) ppm −100.9 (F), MS m/e=213 ($M^+$—$NO_2$), Exact MS Calcd for $C_{10}H_{10}NO_4FS$ ($M^+$) 259.03315, Found 259.0530, Calcd for $C_{10}H_{10}O_2FS$ ($M^+$—$NO_2$) 213.0384, Found 213.0364.

EXAMPLE 2

Into a 100-ml flask were added 1.992 g (12 m moles) of ethyl (ethylthio)fluoroacetate, 50 ml of carbon tetrachloride, 2.136 g (12 m moles) of N-bromosuccinimide and 20 mg of azobisisobutyronitrile in this order, and the flask was filled up with argon gas. The mixture was heated by a sun-lamp for 6 hours with stirring and was refluxed mildly. After cooling the reaction mixture, the insoluble succinimide was filtered and the filtrate was concentrated to obtain 4.94 g of a yellow oily product. The product was purified by silica gel column chromatography (Merck Art 7734, solvent; hexane:ethyl ether=9:1) to obtain 1.250 g (42.5%) of ethyl bromo(ethylthio)fluoroacetate in the form of a light yellow oil.

IR (neat, $cm^{-1}$) 1755 (C=O), $^1$HNMR ($CDCl_3$, TMS) δ 1.33 (3H, t, J=7 Hz, S—$CH_2CH_3$), 1.40 (3H, t, J=7 Hz, $OCH_2CH_3$), 3.05 (2H, q, J=7 Hz, S—$CH_2$), 4.43 (2H, q, J=7 Hz, $OCH_2$), MS m/e=244, 246 ($M^+$), 223, 225 ($M^+$—F), Exact MS Calcd for $C_6H_{10}O_2BrFS$ 243.9570 ($M^+$), Found 2543.9573, Calcd for $C_9H_{10}O_2Br^*FS$ 245.9549 ($M^+$), Found 245.9477, $^{13}$CNMR($CDCl_2$, TMS) ppm 13.9 ($OCH_2CH_3$, $SCH_2CH_3$), 27.0 (S—$CH_2$) 63.9 ($OCH_2$), 99.6 (C—F, $J_{C-F}$=302 Hz), 163.8 (C=O, $J_{C-F}$=24 Hz), $^{13}$FNMR ($CDCl_3$, $CFCl_3$) −81.4 ppm(F).

EXAMPLE 3

Into a 30-ml eggplant type flask were placed 224.2 mg (3.8 m moles) of potassium fluoride and 5 ml of methanol. Thereto was added dropwise 400 mg (1.9 m moles) of benzyl fluoronitroacetate at room temperature with stirring. After completion of the addition, precipitates were collected by filtration and placed into a 100-ml eggplant type flask. Thereto was added 80 ml of tetrahydrofuran. To the mixture was added 549.1 mg (3.8 m moles) of phenylsulfenyl chloride at room temperature with stirring and air in the flask was replaced by argon. The mixture was stirred for 5.5 hours at room temperature and the solvent was removed. To the residue was added 50 ml of ethyl ether and the insolubles were filtered. The filtrate was concentrated to obtain 909 mg of a yellow oily product. The product was purified by silica gel column chromatography (Merck Art 9385, solvent; hexane:ethyl ether=9:1) to obtain 482.5 mg (79.1%) of benzyl fluoronitro(phenylthio)acetate in the form of a colorless oil.

IR (neat, $cm^{-1}$) 1765 (CO), 1580 ($NO_2$), $^1$HNMR ($CDCl_3$, TMS), δ 5.33 (2H, s, $CH_2$), 7.33 (5H, s, $CH_2Ph$), 7.40 (5H, s, SPh), MS m/e=275 ($M^+$—$NO_2$), 199 ($M^+$—$NO_2$—Ph), 167 ($M^+$—$NO_2$—SPh), $^{13}$CNMR($CDCl_3$, TMS) ppm 70.3 ($CH_2$), 113.8 (C—F), 123.5, 128.8, 129.2, 129.8, 131.5, 133.2, 135.8, 136.5 (two kinds of Ar), 159.2 (CO), $^{13}$FNMR($CDCl_3$, $CFCl_3$) ppm −100.8 (F).

EXAMPLE 4

Into a 30-ml eggplant type flask were placed 464 mg (8 m moles) of potassium fluoride and 12 ml of methanol and the mixture was stirred at room temperature. After potassium fluoride dissolved thoroughly, 964 mg (4 m moles) of ethyl nitro(phenylthio)acetate was added dropwise to the mixture. After completion of the addition, precipitates were collected by filtration and placed into a 100-ml eggplant type flask. Thereto was added 70 ml of tetrahydrofuran. To the mixture was introduced perchloryl fluoride gas under cooling with ice. The solvent was removed and 50 ml of ethyl ether was added to the residue. The insolubles were filtered and the filtrate was concentrated to obtain 858 mg of a yellow oily product. The product was purified by column chromatography (Merck Art 9385, solvent; hexane:ethyl ether=9:1) to obtain 497 mg (48.0%) of ethyl fluoronitro(phenylthio)acetate in the form of a yellow oil.

EXAMPLE 5

Into a 10-ml of eggplant type flask were placed 0.245 g (1 m mole) of ethyl bromo(ethylthio)fluoroacetate, 0.650 g (10 m moles) of sodium azide, 2 ml of ethyl acetate, 1 ml of water and 0.5 ml of ethanol. The mixture was stirred for 48 hours at room temperature, while the flask being equipped with an argon gas balloon to prevent the evaporation of the solvent. Water was added to the mixture until sodium azide dissolved thoroughly and the mixture was extracted with ethyl acetate 3 times (5 ml×3). The ethyl acetate layer was washed with a small amount of a saturated aqueous solution of sodium chloride and dried over magnesium sulfate. The solvent was removed to obtain 0.137 g of a light yellow oil. The oil was rather unstable and immediately isolated by preparative chromatography (Merck Art 13792, solvent; hexane:chloroform=3:1) to obtain 0.083 g (40.1%) of ethyl azido(ethylthio)fluoroacetate in the form of a colorless oil.

IR (neat, cm$^{-1}$) 2125 ($N_3$), 1755 (CO), $^1$HNMR(CDCl$_3$, TMS) δ 1.33 (3H, t, J=7 Hz, SCH$_2$CH$_3$), 1.37 (3H, t, J=7 Hz, OCH$_2$CH$_3$), 2.87 (2H, q, J=7 Hz, S—CH$_2$), 4.34 (2H, q, J=7 Hz, OCH$_2$)

$^{13}$CNMR(CDCl$_3$, TMS) ppm 14.0 (SCH$_3$CH$_3$), 14.6 (OCH$_2$CH$_3$), 25.5 (SCH$_2$), 62.5 (OCH$_2$), 95.3 (C—F), 167.4 (C=O), MS m/e=165 (M$^+$—N$_3$), Exact MS Calcd for C$_8$H$_{10}$N$_3$O$_2$FS(M$^+$) 207.0501, Found 207.0490, Calcd for C$_8$H$_{10}$O$_2$FS (M$^+$—N$_3$) 165.0384, Found 165.0371.

EXAMPLE 6

Into a 10-ml of eggplant type flask were placed 0.293 g (1 m mole) of ethyl bromofluoro(phenylthio)acetate, 2 ml of ethyl acetate, 1 ml of water, 0.5 ml of ethanol and 0.65 g (10 m moles) of sodium azide. The mixture was stirred for 28 hours at room temperature, while the flask being equipped with an argon gas balloon. To the reaction mixture was added 10 ml of water and 10 ml of ether and the mixture was extracted. The aqueous layer was further extracted with ethyl ether (10 ml×2). The ether layer was dried over magnesium sulfate and concentrated to obtain 0.221 g of a yellow oil. The oil was purified by preparative chromatography (Merck Art 7748, solvent; hexane:ethyl ether=15:1) to obtain 0.081 g (31.8%) of ethyl azido(phenylthio)fluoroacetate in the form of a light yellow oil.

IR (neat, cm$^{-1}$) 2130 ($N_3$), 1755 (CO), $^1$HNMR (CDCl$_3$, TMS) δ 1.27 (3H, t, J=7 Hz, CH$_3$), 4.28 (2H, q, CH$_2$), 7.2~7.8 (5H, m, Ar)

$^{13}$CNMR(CDCl$_3$, TMS) ppm 14.0 (CH$_3$), 62.7 (CH$_2$), 94.2 (C—F), 127.5, 129.1, 130.7, 137.1 (Ar), 166.1 (C=O), MS m/e=213 (M$^+$—N$_3$), Exact MS Calcd for C$_{10}$H$_{10}$N$_3$O$_2$FS(M$^+$) 255.0478, Found 255.0709, Calcd for C$_{10}$H$_{10}$O$_2$FS (M$^+$—N$_3$) 213.0384, Found 213.0382.

EXAMPLE 7

Into a 30-ml eggplant type flask were placed 0.521 g (1.97 m moles) of ethyl dibromofluoroacetate, 1 ml of methylene chloride, 1.292 g (19.8 m moles) of sodium azide, 0.297 g (0.92 m mole) of tetra-n-butylammonium bromide and 1 ml of water. The mixture was stirred for 6 days at room temperature, while the flask being equipped with an argon gas balloon. The insoluble sodium azide and sodium bromide were removed by filtration and the organic layer was separated with use of a separating funnel. The aqueous layer was saturated with sodium chloride and extracted twice with 5 ml of methylene chloride. The methylene chloride layers were combined and dried over magnesium sulfate. The solvent was removed to obtain 0.340 g of a brown oil. The oil was purified by column chromatography (Merck Art 9385, solvent; hexane:ethyl ether=2:1) to obtain 0.209 g (46.9%) of ethyl azidobromofluoroacetate in the form of a colorless oil.

IR (neat, cm$^{-1}$) 2140 ($N_3$), 1760 (C=O), $^1$HNMR (CDCl$_3$, TMS) δ 1.37 (3H, t, J=7 Hz, CH$_3$), 4.37 (2H, q, J=7 Hz, CH$_2$), $^{13}$CNMR(CDCl$_3$, TMS) ppm 14.1 (CH$_3$), 64.6 (CH$_2$), 89.8 (C—F), 163.1 (C=O), MS m/e=183, 185 (M$^+$—N$_3$)

Reference Example 1

To 150 ml of tetrahydrofuran (THF) were added 6.5 g (0.1 mole) of pulverized EtONa and 11.1 g (0.1 mole) of thiophenol and the mixture was refluxed for 10 minutes. Thereto was added 18.5 g (0.1 mole) of ethyl fluorobromoacetate and the mixture was refluxed for one hour with stirring. THF was removed by an evaporator and the precipitated NaBr was filtered. The organic layer was washed with water, dried and distilled to obtain 19.2 g (90%) of ethyl fluoro(phenylthio)acetate.

IR (neat, cm$^{-1}$) 1760 (C=O), $^{19}$FNMR (CDCl$_3$, CFCl$_2$) ppm —158.7(d), J=53.7, $^{13}$CNMR(CDCl$_3$, TMS) ppm 94.2 (dd), J$_{C-F}$=235 Hz, 110 (C—H), 165.3 (d), J=26.0.

What is claimed is:

1. A fluorine-containing multi-functional ester compound of the formula:

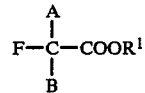

wherein A is NO$_2$, Br or N$_3$, B is C$_6$H$_5$S or C$_2$H$_5$S, provided that when A is N$_3$ then B may also be Br, R$^1$ is selected from the group consisting of alkyl of 1 to 4 carbon atoms, phenyl, chlorophenyl, tolyl, xylyl, naphthyl, benzyl and phenethyl.

2. A fluorine-containing multi-functional ester compound of the formula:

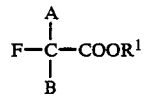

wherein A is NO$_2$, B is C$_6$H$_5$S and R$^1$ is alkyl of 1 to 4 carbon atoms.

* * * * *